(12) United States Patent  
Groh et al.

(10) Patent No.: US 7,110,494 B2  
(45) Date of Patent: *Sep. 19, 2006

(54) X-RAY DIAGNOSTIC APPARATUS WITH A PATIENT WEIGHTING DEVICE ASSOCIATED WITH THE PATIENT POSITIONING TABLE

(75) Inventors: Burkhard Groh, Chicago, IL (US); Volker Heer, Gundelsheim (DE); Mathias Hörnig, Erlangen (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/896,656

(22) Filed: Jul. 22, 2004

(65) Prior Publication Data

US 2005/0053195 A1    Mar. 10, 2005

(30) Foreign Application Priority Data

Jul. 22, 2003    (DE) .................. 103 33 294

(51) Int. Cl.
*H05G 1/10*    (2006.01)
(52) U.S. Cl. ...................................... 378/95
(58) Field of Classification Search .............. 378/62, 378/64, 95, 101, 108, 114–117, 165, 208, 378/209
See application file for complete search history.

(56) References Cited

U.S. PATENT DOCUMENTS 6,035,227 A * 3/2000 Shmueli ............... 600/425
6,370,425 B1 * 4/2002 Oguma ................. 600/547

FOREIGN PATENT DOCUMENTS

DE    OS 198 09 738    9/1999
DE    OS 101 18 183    11/2002

* cited by examiner

*Primary Examiner*—Courtney Thomas
(74) *Attorney, Agent, or Firm*—Schiff Hardin LLP

(57) ABSTRACT

An x-ray diagnostic apparatus has an x-ray radiator, a control device connected thereto, a radiation detector and a patient positioning table. A patient weighing device that is connected with the control device to influence parameters for setting the x-ray radiation is associated with the patient positioning table.

6 Claims, 2 Drawing Sheets

X-RAY DIAGNOSTIC APPARATUS WITH A PATIENT WEIGHTING DEVICE ASSOCIATED WITH THE PATIENT POSITIONING TABLE

BACKGROUND OF THE INVENTION

1. Field of the Invention

The present invention concerns an x-ray diagnostic apparatus of the type having an x-ray radiator, a control device connected thereto, a radiation detector and a patient positioning table.

2. Description of the Prior Art

In modern medical systems such as, for example, cardio systems, angiography systems or computed tomography systems, current patient data such as, for example, pulse, blood pressure etc. are only considered in part. An optimal adaptation of the generator settings for the respective applications to the patient thickness, however, is desired. Therefore, the system should be adaptable as flexibly as possible to the respective patient in order to achieve an optimally low radiation exposure of the patient.

From German OS 198 09 738, an x-ray diagnostic apparatus is known with a control unit to preset the radiation diaphragm setting necessary for the image acquisition, the control unit being provided with a computer that, based on direct access to patient data, makes a calculation for a presetting adapted to the patient, and adjusts the optimal diaphragm value by motors. An optimum adaptation of the generator settings to the patient thickness does not ensue in this known x-ray diagnostic apparatus.

Data such as the patient thickness can be taken from patient records, and thus can significantly deviate from the true current data. Often such data are not determined and used at all, but rather are only roughly estimated. Generally, a number of operating programs known as organ programs are available, with which the desired values for thin or thick patients are selected.

SUMMARY OF THE INVENTION

An object of the present invention is to provide an x-ray diagnostic apparatus of the initially described type, wherein an optimally comprehensive automated adjustment of suitable system data ensues.

The object is inventively achieved by the use of a patient-weighing device, connected with the control device to influence parameters determining the x-ray radiation that is associated with the patient-positioning table. With the automatic detection of weight and fat ratio of the patient at the beginning of a treatment, an optimal adaptation of the system parameters that are suitable for the adjustment of the suitable system data (such as, for example, the generator parameters) for the radiation dose ensues for the patient.

Preferably the weighing device is provided with a device for body fat analysis.

The weighing device and/or the device for body fat analysis are integrated into the patient positioning table.

An evaluation device that determines the optimum parameters for the control device from the weight and body fat ratio can inventively be connected to the weighing device.

The control device (voltage generator) can include an organ program bank connected to the evaluation device. Further data such as the age of the patient and other information can be entered into the organ program bank, so that an appropriate organ program can be selected based on the parameters determined by the evaluation device and on the further information entered into the organ program bank.

The data automatically determined by the weighing device can be supplied to the hospital information system (HIS) for the electronic patient record.

DESCRIPTION OF THE PREFERRED EMBODIMENTS

Figure 1:
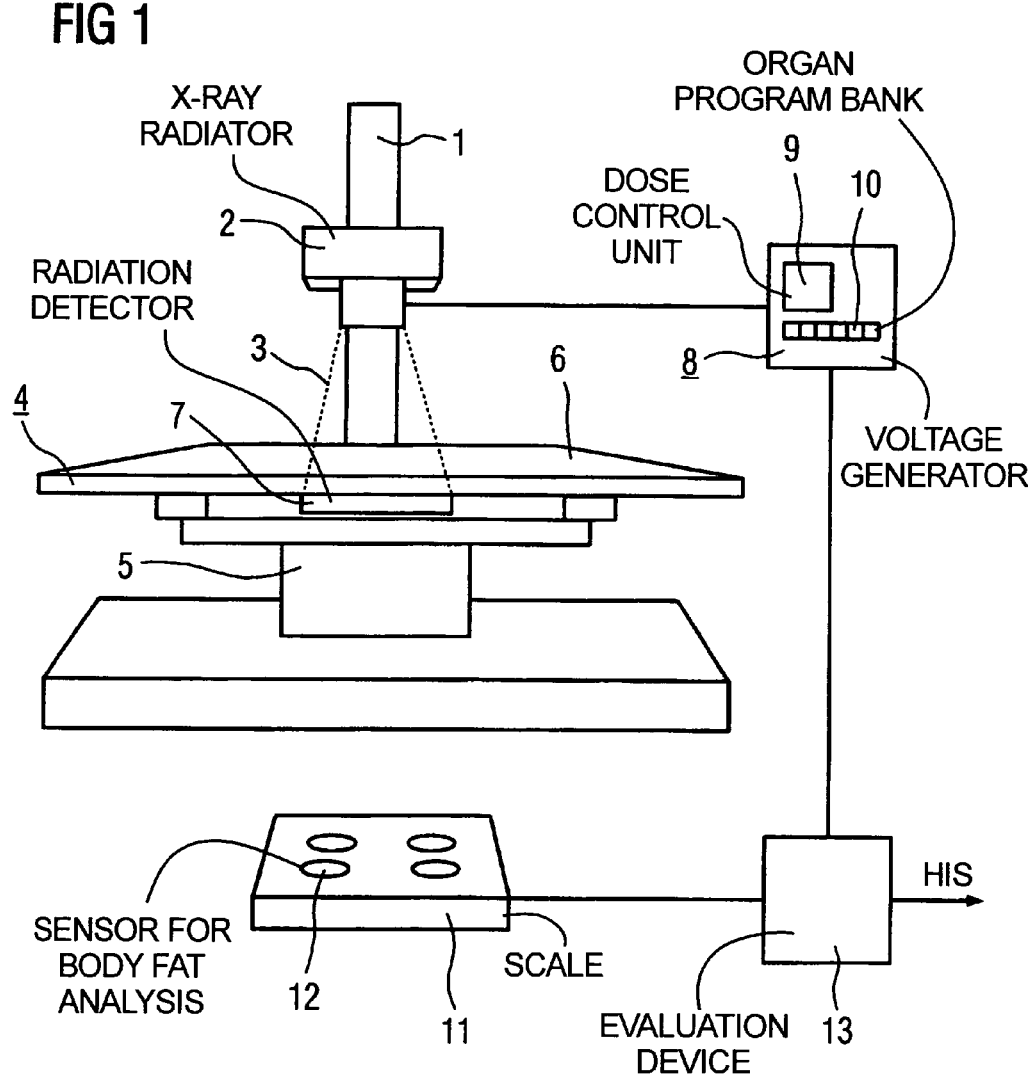
FIG. 1 illustrates an x-ray apparatus with an inventive device to determine weight and body fat ratio.

In FIG. 1, an x-ray diagnostic apparatus is shown that has an x-ray radiator 2 mounted on a stand 1 as an x-ray source that generates an x-ray beam 3 directed downwardly. A displaceably mounted patient positioning table 4 is attached to a base 5. A detector 7 (for example a digital solid-state planar detector, an x-ray image intensifier television chain, or an x-ray film cassette) is displaceably arranged under the positioning plate 6 of the patient positioning table 4.

A voltage generator 8 with a dose control unit 9 that can include an organ program bank 10 is connected with the x-ray radiator 2.

Associated with the x-ray diagnostic apparatus is a scale as a weighing device that can be equipped with sensors 12 for body fat analysis. The scale 11 is connected with an evaluation device 13 that transmits the values of the weight and the body fat ratio of the patient to the dose control unit 9, such that a patient-specific organ program adaptation can ensue. For example, via the organ program bank 10 further data, such as the age of the patient, can additionally be entered.

The evaluation device 13 can be connected with a hospital information system (HIS) to which the measured data are supplied for storage in the electronic patient record (EPR).

Figure 2:
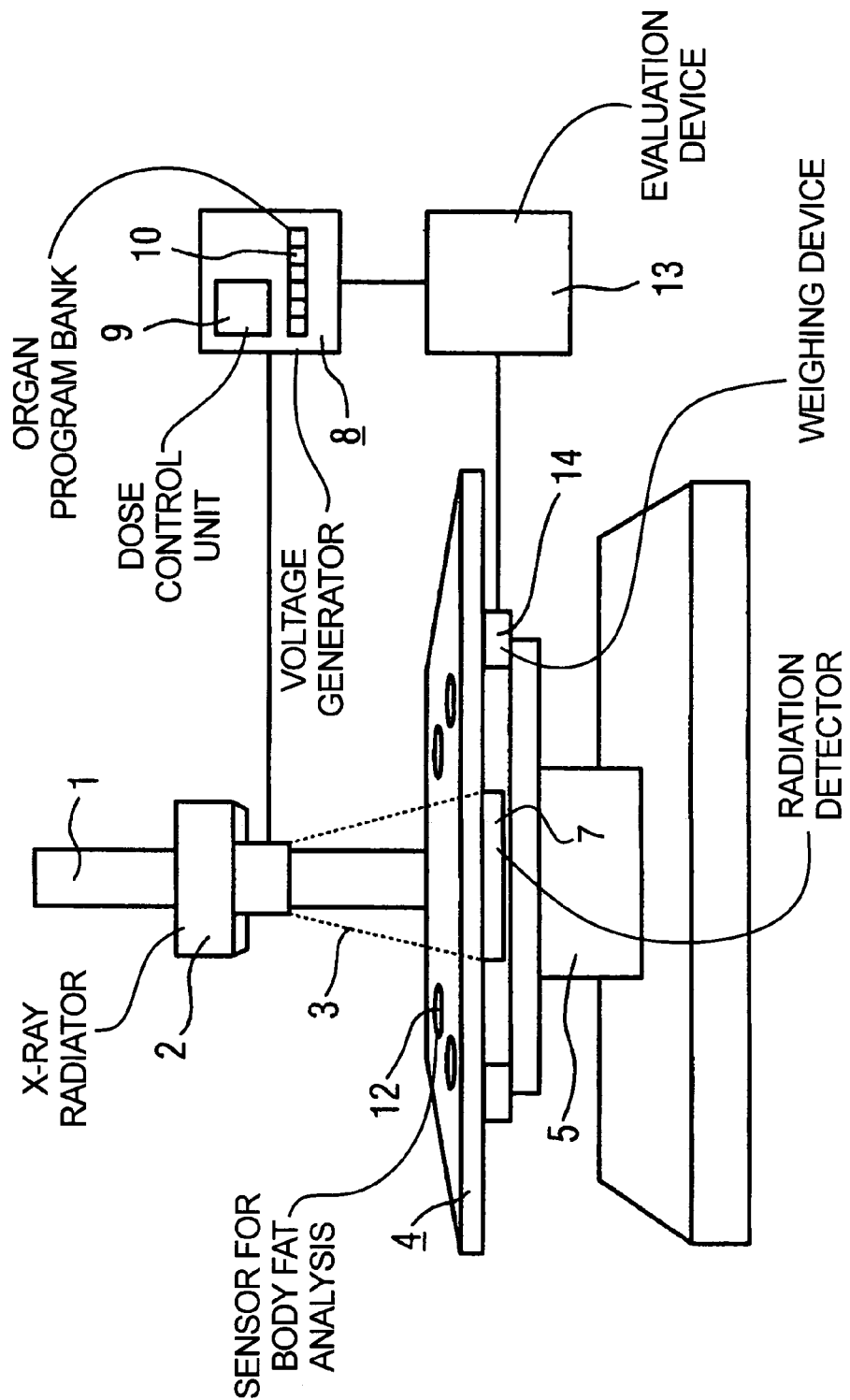
FIG. 2 illustrates a further embodiment of an inventive x-ray apparatus with an integrated device to determine weight and body fat ratio.

A further embodiment of the inventive x-ray diagnostic apparatus is shown in FIG. 2, in which a weighing device 14 is integrated into the patient positioning table 4 instead of the separately arranged scale 11. This can, for example, be realized by strain gauges (not shown). Furthermore, the surface of the positioning plate 6 embodies sensors 12 for body fat analysis. The weighing device 14 is, as already specified, connected with the evaluation device 13 for correction of the generator data of the organ program bank 10.

Each x-ray system thus is equipped with a weighing device 11 or 14 that, for example, can be integrated into the patient positioning table 4. Additionally, the scale 11 itself can incorporate a body fat analysis function. The sensors 11 to detect the values for this function also can be integrated into the patient positioning table 4.

By automatic detection of weight and fat ratio of the patient at the beginning of a treatment, it is possible to automatically adapt the system parameters to the patient. From the weight and body fat ratio, the evaluation device 13 can determine the optimum parameters for the treatment and transfer them to the dose control unit 9 of the system. Further data, such as age, etc. can likewise be taken into account. A patient-specific organ program adaptation is achieved that ensures a low dose exposure for the patient. At the same time, the image quality can be improved because the tissue property (meaning the ratio of fat to muscle tissue) can be taken into account in determining the absorption of the radiation. Furthermore, the automatically determined data of weight and body fat ratio can be provided to the patient information system of the hospital for the electronic patient record.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostic apparatus comprising:
   an x-ray radiator operable to emit x-rays;
   a control device connected to the x-ray radiator for controlling the emission of x-rays from said x-ray radiator;
   a patient positioning table adapted to receive a patient thereon for irradiation by said x-rays; and
   a weighing device associated with the patient positioning table, and connected to said control device, adapted to interact with a patient on said patient positioning table for identifying the weight of the patient said weighing device including a device for performing body fat analysis of a patient on the patient positioning table to obtain a body fat value of the patient, supplying said weight and said body fat value to the control device, said control device controlling the emission of said x-rays from said x-ray radiator dependent on said weight and said body fat value.

2. An x-ray diagnostic apparatus as claimed in claim 1 wherein said weighing device is built into the patient-positioning table.

3. An x-ray diagnostic apparatus as claimed in claim 1 comprising an evaluation device connected between said control device and said weighing device for determining optimum parameters for the emission of said x-rays from said weight, and for supplying said optimum parameters to said control device.

4. An x-ray diagnostic apparatus as claimed in claim 3 wherein said evaluation device comprises an organ program bank connected to said evaluation device, said organ program bank supplying an organ program to said control device dependent on said parameters from said evaluation device.

5. An x-ray diagnostic apparatus as claimed in claim 4 comprising an input unit or entering data relating to the patient on the position table into said organ program bank, and said organ program bank selecting said organ program dependent on said optimum parameters and said data.

6. An x-ray diagnostic apparatus as claimed in claim 1 comprising a communication interface to a hospital information system for allowing said weight determined by said weighing device to be supplied to said hospital information system for inclusion in an electronic patient record of the patient on the patient-positioning table.

* * * * *